US009550721B2

(12) United States Patent
Li et al.

(10) Patent No.: US 9,550,721 B2
(45) Date of Patent: Jan. 24, 2017

(54) METHOD FOR PREPARING DIMETHYL 1,4-CYCLOHEXANEDICARBOXYLATE AND METHOD FOR PREPARING 1,4-CYCLOHEXANEDIMETHANOL

(71) Applicant: China Petrochemical Development Corporation, Taipei (TW)

(72) Inventors: Wei-Ying Li, Taipei (TW); Shih-Yao Chao, Taipei (TW); I-Hui Lin, Taipei (TW)

(73) Assignee: China Petrochemical Development Corporation, Taipei (TW)

( * ) Notice: Subject to any disclaimer, the term of this patent is extended or adjusted under 35 U.S.C. 154(b) by 0 days.

(21) Appl. No.: 14/831,228

(22) Filed: Aug. 20, 2015

(65) Prior Publication Data
US 2016/0326088 A1 Nov. 10, 2016

(30) Foreign Application Priority Data

May 6, 2015 (TW) .............................. 104114372 A

(51) Int. Cl.
*C07C 69/74* (2006.01)
*C07C 67/303* (2006.01)
*C07C 29/149* (2006.01)

(52) U.S. Cl.
CPC ........... *C07C 67/303* (2013.01); *C07C 29/149* (2013.01)

(58) Field of Classification Search
CPC ............................... C07C 67/33; C07C 29/149
USPC .......................................... 560/127
See application file for complete search history.

(56) References Cited

U.S. PATENT DOCUMENTS 3,027,398 A * 3/1962 Foohey ................. C07C 67/303
  502/185
3,334,149 A 8/1967 Akin et al.

FOREIGN PATENT DOCUMENTS

| CN | 1689698 A | 11/2005 |
| CN | 102796001 A | 11/2012 |
| TW | 565469 B | 12/2003 |

OTHER PUBLICATIONS

Abstract of TW565469.*

* cited by examiner

*Primary Examiner* — Deborah D Carr
(74) *Attorney, Agent, or Firm* — Mintz Levin Cohn Ferris Glovsky and Popeo, P.C.; Peter F. Corless; Richard B. Emmons

(57) ABSTRACT

A method for preparing dimethyl 1,4-cyclohexanedicarboxylate (DMCD) is provided. The method includes hydrogenating dimethyl terephthalate (DMT) under a condition of a pressure of 20 to 30 $kg/cm^2$ to continuously prepare the DMCD, and thereby increasing the selectivity of the DMCD. A method for preparing 1,4-cyclohexanedimethanol (CHDM) is further provided.

12 Claims, No Drawings

METHOD FOR PREPARING DIMETHYL 1,4-CYCLOHEXANEDICARBOXYLATE AND METHOD FOR PREPARING 1,4-CYCLOHEXANEDIMETHANOL

CROSS-REFERENCES TO RELATED APPLICATIONS

This application claims under 35 U.S.C. §119(a) the benefit of Taiwanese Application No. 104114372, filed May 6, 2015, the entire contents of which are incorporated herein by reference.

BACKGROUND OF THE INVENTION

1. Field of the Invention

The present invention relates to hydrogenation reactions, more particularly, to a method for preparing dimethyl 1,4-cyclohexanedicarboxlate (DMCD) by a hydrogenation reaction.

2. Description of Related Art 1,4-cyclohexanedimethanol (CHDM) is widely used for condensing monomers of a polymer and a unique polyester. DMCD is an intermediate during the synthesis of CHDM, and plays an important role in the synthesis of CHDM.

Usually, the preparation of DMCD involves the use of dimethyl terephthalate (DMT) as a starting material, and then two different types of hydrogenation reactions sequentially take place (i.e., the hydrogenation of a benzene backbone and the hydrogenation of an ester). The hydrogenation of the benzene backbone of DMT generates DMCD, and then the hydrogenation of the ester of DMCD generates CHDM.

The hydrogenation catalysts added in the above two steps are different, wherein the catalysts used as the hydrogenation catalysts for a benzene backbone have gradually progressed from the earlier used palladium-based catalysts to the current ruthenium-based catalysts. When a palladium-based catalyst is used, a higher pressure and a higher temperature (e.g., from 140 to 400° C.) are required. Further, the palladium-based catalyst is likely to be poisoned by CO as a by-product of the reaction. On the contrary, a ruthenium-based catalyst can react at a lower pressure (e.g., from 10 to 175 bars) and a lower temperature range (e.g., from 150 to 230° C.), and is not poisoned by the CO by-product. However, the ruthenium-based catalyst is likely to be inactivated, leading to shorter lifetime and lower yield.

U.S. Pat. No. 3,334,149 firstly discloses a palladium-based catalyst, which requires a pressure of 340 bars. Subsequently, CN1099382 discloses the control of the palladium content, dispersibility, depth of the surface, and the crystalline phase of $Al_2O_3$ in a $Pd/Al_2O_3$ catalyst lowers the reaction pressure to 125 bars.

Moreover, it has been reported that a metal of group VIIIB or IIA is added as a second component or a metal selected from group VIIIB, $Ti^{4+}$, $Zr^{4+}$, $Sn^{4+}$, $Mn^{4+}$ and $Cr^{4+}$ is added as a third component to increase activity of hydrogenation. CN1099745 discloses that a metal of group VIIIB, such as one of Ni, Ru and Pt, is added as a second component to increase the activity of hydrogenation, and can lower the reaction pressure to 125 bars. CN102381976 discloses that the addition of a catalyst with magnesium (Mg) as a second component, and one or more tetravalent metals ($M^{4+}$) selected from $Ti^{4+}$, $Zr^{4+}$, $Sn^{4+}$, $Mn^{4+}$ and $Cr^{4+}$ as a third component can lower the reaction temperature to 70 bars.

U.S. Pat. No. 3,334,149 firstly discloses a ruthenium-based catalyst. The catalyst is $Ru/Al_2O_3$, and can catalyze hydrogenation at 160° C. and 50 bars. TW565469 discloses the use of different catalysts for hydrogenation reactions in a method can increase the reaction activity, and carries out the hydrogenation reactions at pressures of from 48.26 to 55.1 bars. CN102796001 discloses that hydrogenation can take place at 40 bars by using DMCD as a solvent. CN1689698 discloses that hydrogenation can take place at 40 bars by using Si as a first auxiliary and Ru as a second auxiliary. CN1915962 discloses that hydrogenation reactions can take place as batches at 30 bars by altering the metal contents and using a solvent.

The above patents show that if a palladium-based catalyst is used during the process of generating DMCD from DMT, hydrogenation reactions need to take place in a high pressure environment. The buildup cost and operational fee of a factory for the reactions are very high. By the use of a ruthenium-based catalyst, the reaction pressure and the production cost are reduced at the same time. However, a continuous hydrogenation reaction cannot take place at a pressure of lower than 40 bars.

Accordingly, there still exists a need to develop a method for preparing DMCD by a continuous hydrogenation reaction at a lower pressure.

SUMMARY OF THE INVENTION

The present invention provides a method for preparing DMCD, including hydrogenating DMT in a reactor containing a $Ru/Al_2O_3$ catalyst to prepare the DMCD, wherein the pressure in the reactor is from 20 to 30 $kg/cm^2$ (i.e., from 9.81 to 29.43 bars), and the liquid hourly space velocity (LHSV) of the DMT is from 2 to 8 $hours^{-1}$.

The present invention further provides a method for preparing CHDM, including hydrogenating DMT in a first reactor containing a $Ru/Al_2O_3$ catalyst to continuously form DMCD, wherein the pressure in the first reactor is from 20 to 30 $kg/cm^2$, and the LHSV of DMT is from 2 to 8 $hours^{-1}$; and charging the DMCD into a second reactor to hydrogenate an ester group of the DMCD.

The present invention employs a ruthenium catalyst as an active component, instead of the more expensive rare palladium metal. At the same time, the technical bottleneck of not being able to perform continuous hydrogenation at a pressure lower than 40 bars in the state-of-art can be overcome. As such, the safety can be significantly increased and the operational fee can be saved, and thereby bringing about economical benefits in the industrial standard. In addition, the method of the present invention is still able to achieve a high conversion rate of DMT and high DMCD selectivity even under a low pressure.

DETAILED DESCRIPTION OF THE PREFERRED EMBODIMENTS

The following specific embodiments are used to illustrate the detailed description of the present invention, but the claims of the present invention are not restricted thereto. The present invention can also be implemented or applied by other different ways. Each of the details in the present specification can be modified or altered in any way based on different aspects and applications, without departing from the spirit of the disclosure of the present invention.

The present invention provides a method for preparing DMCD, including hydrogenating DMT in a reactor containing a $Ru/Al_2O_3$ catalyst to continuously prepare the DMCD, wherein the pressure in the reactor is from 20 to 30 $kg/cm^2$ (i.e., from 9.81 to 29.43 bars), and the liquid hourly space velocity (LHSV) of DMT is from 2 to 8 hours$^{-1}$.

In the preparation of DMCD, the reactor can be either a batch reactor or a continuous reactor, depending upon the operation. The batch reactor refers a reactor used for charging once before a reaction, and discharging once after the completion of the reaction. The continuous reactor refers to a reactor used for continuously charging, continuously reacting, and continuously discharging.

In the present invention, a trickle bed reactor (which is a tri-phase reactor) is used, particularly a type of reactor in which a granular solid catalyst bed through which gas and liquid move in a cocurrent flow for a tri-phase reaction of gas, liquid and solid is used. The reactor has the advantages of being a simple structure and having a low equipment cost and the feature of allowing an easy and flexible operation. Therefore, the trickle fluid bed reactor has a wide range of applications in the fields of oil refining and chemical engineering. In particular, the trickle fluid bed reactor is one of the most basic reactors used in the fields of cracking oil products by hydrogenation and refining hydrocarbons by hydrogenation.

If reactors are distinguished by the approach for delivering reaction materials, they can be classified into fixed-bed reactors and fluidized-bed reactors. Fixed-bed reactors are also referred to as packed bed reactors, each of which is packed with a solid catalyst or a solid reactant, and used as a reactor for carrying out a multi-phase reaction. A solid is usually granular, and has a particle diameter of from about 2 to 15 mm The solids stack to form a bed with a certain height (or thickness). The bed is immobile, and a fluid passes through the bed for a reaction to take place. The fluidized-bed reactor is distinguished from the fixed-bed reactor in that the solid particles are not immobile.

The catalysts in a fluidized-bed reactor are not limited to be granular. Mesh catalysts have already been applied industrially. Currently, honeycomb and fibrous catalysts have also been widely used.

The catalysts in a trickle bed reactor can exist in the form of a fixed bed. Thus, this type of reactor can also be regarded as a type of a fluidized-bed reactor.

In an embodiment of the method for preparing DMCD, the reactor is a fixed-bed reactor.

Usually, in the method for preparing DMCD, DMT is dissolved in a solvent. The solvent can be methyl acetate, ethyl acetate, propyl acetate, butyl acetate, or at least one selected from the group consisting of the foregoing. In an example, the solvent is ethyl acetate.

In another embodiment of the method for preparing DMCD, the reaction temperature of hydrogenation is lower than 230° C. The temperature of hydrogenation is usually from 100 to 180° C., preferably from 120 to 160° C. Specifically, in a fixed-bed reactor containing a Ru/Al$_2$O$_3$ catalyst, DMT is hydrogenated at a temperature of from 100 to 180° C. or from 120 to 160° C.

In an example, the LHSV of DMT is from 2 to 8 hours$^{-1}$.

Moreover, according to the aforesaid method, a method for preparing CHDM is further provided, which includes hydrogenating DMT in a first reactor containing a Ru/Al$_2$O$_3$ catalyst to continuously form DMCD, wherein the pressure in the first reactor is from 20 to 30 kg/cm$^2$; and charging the DMCD into a second reactor to hydrogenate an ester group of the DMCD.

The second reactor can also be a fixed-bed reactor. Further, in the second hydrogenation reaction, the catalyst used can be a copper catalyst having a manganese co-catalyst, the molar ratio of a hydrogen gas to a reactant can be from 200:1 to 1000:1. Relevant conditions can be referred to the content of CN1109859.

In the following examples, LHSV, conversion rate of DMT and selectivity of DMCD are defined as follows.

LHSV=DMT (mL/h)/catalyst (mL)

Conversion rate of DMT=number of moles of DMT consumed/number of moles of DMT added× 100%

Selectivity of DMCD=number of moles of DMCD generated/number of moles of DMT consumed× 100%

In the following examples, the DMT used was purchased from Acros Company, and ethyl acetate (EA) is purchased from ECHO Company.

EXAMPLE 1

DMT was continuously hydrogenated to generate DMCD.

Firstly, a Ru/Al$_2$O$_3$ globular catalyst (the weight of the packed catalyst was 78 g, and the volume of the catalyst was 57.51 mL) containing 1.5 wt % of Ru was added to a fixed-bed reactor. A mixed solution of DMT and EA and hydrogen gas were charged separately into the upper portion of the reactor. The reaction took place under the conditions of a pressure of 10 kg/cm$^2$, a reaction temperature of 140° C., a flow speed of hydrogen gas of 300 ccm, a concentration of DMT of 3.5 wt % in the charged mixed solution of DMT and EA, and LHSV=2 h$^{-1}$. Upon completion of the reaction, the product was discharged from the lower portion of the reactor. The conversion rate of DMT was 64.6%, and the selectivity of DMCD was 92.8%.

EXAMPLE 2

Hydrogenation was carried out under the conditions in example 1 to produce DMCD. However, the difference between examples 1 and 2 was that the pressure was increased to 20 kg/cm$^2$ in example 2. Upon completion of the reaction, the product was discharged from the bottom of the reactor. The conversion rate of DMT was 99.9%, and the selectivity of DMCD was 99.9%.

EXAMPLE 3

Hydrogenation was carried out under the conditions in example 1 to produce DMCD. However, the difference between examples 1 and 3 was that the pressure was increased to 30 kg/cm$^2$ in example 3. Upon completion of the reaction, the product was discharged from the bottom of the reactor. The conversion rate of DMT was 100.0%, and the selectivity of DMCD was 100.0%.

EXAMPLE 4

Hydrogenation was carried out under the conditions in example 1 to produce DMCD. However, the difference between examples 1 and 4 was that the pressure was increased to 40 kg/cm$^2$ in example 4. Upon completion of the reaction, the product was discharged from the bottom of the reactor. The conversion rate of DMT was 100.0%, and the selectivity of DMCD was 97.3%.

EXAMPLE 5

Hydrogenation was carried out under the conditions in example 1 to produce DMCD. However, the differences between examples 1 and 5 are that the pressure were increased to 20 kg/cm² and the reaction temperature was decreased to 120° C. in example 5. Upon completion of the reaction, the product was discharged from the bottom of the reactor. The conversion rate of DMT was 94.8%, and the selectivity of DMCD was 100.0%.

EXAMPLE 6

Hydrogenation was carried out under the conditions in example 1 to produce DMCD. However, the differences between examples 1 and 6 were that the pressure was increased to 20 kg/cm² and the reaction temperature was increased to 180° C. in example 6. Upon completion of the reaction, the product was discharged from the bottom of the reactor. The conversion rate of DMT was 100.0%, and the selectivity of DMCD was 97.3%.

EXAMPLE 7

Hydrogenation was carried out under the conditions in example 1 to produce DMCD. However, the differences between examples 1 and 7 were that the pressure was increased to 20 kg/cm² and the LHSV was increased to 8 h⁻¹ in example 7. Upon completion of the reaction, the product was discharged from the bottom of the reactor. The conversion rate of DMT was 98.3%, and the selectivity of DMCD was 99.6%.

The present invention employs a ruthenium catalyst as an active component, instead of the more expensive rare palladium metal. At the same time, the technical bottleneck of not being able to perform continuous hydrogenation at a pressure lower than 40 bars in the state-of-art can be overcome. As such, the safety can be significantly increased and the operational fee can be saved, and thereby bringing about economical benefits in the industrial standard. In addition, the method of the present invention is still able to achieve a high conversion rate of DMT and high DMCD selectivity even under a low pressure.

The above examples are provided only to illustrate the principle and effect of the present invention, and they do not limit the scope of the present invention. One skilled in the art should understand that, modifications and alterations can be made to the above examples, without departing from the spirit and scope of the present invention. Therefore, the scopes of the present disclosure should be accorded to the disclosure of the appended claims.

The invention claimed is:

1. A method for preparing dimethyl 1,4-cyclohexanedicarboxylate (DMCD), comprising: hydrogenating dimethyl terephthalate (DMT) in a reactor containing a Ru/Al$_2$O$_3$ catalyst to continuously form the DMCD, wherein a pressure in the reactor is from 20 to 30 kg/cm², and a liquid hourly space velocity (LHSV) of the DMT is from 2 to 8 hours⁻¹.

2. The method of claim 1, wherein the reactor is a fixed-bed reactor.

3. The method of claim 1, wherein the DMT is dissolved in a solvent.

4. The method of claim 3, wherein the solvent is at least one selected from the group consisting of methyl acetate, ethyl acetate, propyl acetate and butyl acetate.

5. The method of claim 1, wherein the step of hydrogenating is conducted at a temperature of from 100 to 180° C.

6. The method of claim 1, wherein the step of hydrogenating is conducted at a temperature of from 120 to 160° C.

7. A method for preparing 1,4-cyclohexanedimethanol (CHDM), comprising: hydrogenating dimethyl terephthalate (DMT) in a first reactor containing a Ru/Al$_2$O$_3$ catalyst to continuously form the dimethyl 1,4-cyclohexanedicarboxylate (DMCD), wherein a pressure in the first reactor is from 20 to 30 kg/cm², and a liquid hourly space velocity (LHSV) of DMT is from 2 to 8 hours⁻¹; and
charging the DMCD into a second reactor to hydrogenate an ester group of the DMCD.

8. The method of claim 7, wherein the first reactor is a fixed-bed reactor.

9. The method of claim 7, wherein the DMT is dissolved in a solvent.

10. The method of claim 9, wherein the solvent is at least one selected from the group consisting of methyl acetate, ethyl acetate, propyl acetate, and butyl acetate.

11. The method of claim 7, wherein the step of hydrogenating in the first reactor is conducted at a temperature of from 100 to 180° C.

12. The method of claim 7, wherein the step of hydrogenating in the first reactor is conducted at a temperature of from 120 to 160° C.

* * * * *